United States Patent [19]

Ohno et al.

[11] Patent Number: 5,336,827
[45] Date of Patent: Aug. 9, 1994

[54] PROCESS FOR PRODUCING AN OLIGOMER

[75] Inventors: Takashi Ohno; Toshiyuki Tsubouchi, both of Sodegaura, Japan

[73] Assignee: Idemitsu Kosan Co., Ltd., Tokyo, Japan

[21] Appl. No.: 78,822

[22] Filed: Jun. 21, 1993

[30] Foreign Application Priority Data

Jul. 9, 1992 [JP] Japan .................................. 4-182379
Jul. 9, 1992 [JP] Japan .................................. 4-182395

[51] Int. Cl.$^5$ .......................... C07C 2/02; C07C 7/00; C07C 7/10
[52] U.S. Cl. .................................. 585/502; 585/518; 585/519; 585/809; 585/810; 585/833
[58] Field of Search .............. 585/518, 519, 809, 810, 585/833, 502

[56] References Cited

U.S. PATENT DOCUMENTS 3,492,366  1/1970  Winter .................................. 585/519
5,177,282  1/1993  Nierlich et al. ...................... 585/519

FOREIGN PATENT DOCUMENTS 0305807   3/1989  European Pat. Off. .
0402881  12/1990  European Pat. Off. .
0508292  10/1992  European Pat. Off. .

Primary Examiner—Anthony McFarland
Assistant Examiner—Nhat D. Phan
Attorney, Agent, or Firm—Oblon, Spivak, McClelland, Maier & Neustadt

[57] ABSTRACT

There are disclosed a process for producing an oligomer by oligomerizing a raw material comprising an unsaturated bicyclo heptane derivative and/or an unsaturated bicyclo octane derivative, which comprises the step of restricting the contents of dienes contained in the raw material to at most 1% by weight; and a process wherein the raw material is subjected to solid acid treatment simultaneously with or prior to distillation and then to oligomerization. The above process can efficiently produce the oligomer well suited for use in a traction drive fluid having a low viscosity and exhibiting excellent performance over a wide temperature range.

9 Claims, No Drawings

PROCESS FOR PRODUCING AN OLIGOMER

BACKGROUND OF THE INVENTION

1. Field of the Invention

The present invention relates to a process for producing an oligomer. More particularly, it relates to a process for efficiently producing an oligomer suitable for use in a hydrocarbon-based traction drive fluid, which has good flowability at low temperatures and exhibits high performance in a wide temperature range from low to high temperatures.

2. Description of the Related Arts

Generally, traction drive fluids are used in traction drive units (friction driving equipment utilizing rolling contact), for example, continuously variable transmission for automobiles, continuously variable transmission for industrial purposes, and hydraulic machines. As the demands for drive fluids have increased, it is required that traction drive fluids should have a high traction coefficient, good stability to heat and oxidation and a high economical efficiency.

In recent years, attempts have been made to construct small-sized and lightweight traction drive units for the sake of, mainly, the automobile use. Therefore, traction drive fluids to be used in the traction drive units are required to have performance capable of withstanding the use under various severe conditions, particularly to exhibit high performance (e.g., a high traction coefficient, a low viscosity, and good stability to heat and oxidation) reliably over a wide temperature range from low to high temperatures (approximately −30° to +140° C.).

Various traction drive fluids have heretofore been proposed in, for example, Japanese Patent Publication Nos. 46(1971)-338, 46(1971)-339, and 61(1986)-44918. However, any of these proposed traction drive fluids cannot satisfy the requirements described above and have various problems. For example, a compound exhibiting a high traction coefficient at high temperatures has the drawbacks in that it causes large churning loss to occur due to its high viscosity, and therefore the transmission efficiency is low, and in that starting characteristics at low temperatures are bad. A compound having a low viscosity and a high transmission efficiency has the drawbacks in that the traction coefficient at high temperatures is markedly low, in that the viscosity becomes markedly low at high temperatures and causes a trouble in lubrication of the traction drive units.

In view of the above circumstances, the research group of the inventors carried out study to eliminate the problems of the conventional techniques and found that a hydrogenated oligomer of an unsaturated bicyclo heptane derivative (which is proposed in Japanese Patent Application Laid-Open No. 3(1991)-95295) and a hydrogenated oligomer of an unsaturated bicyclo octane derivative (which is proposed in Japanese Patent Application Laid-Open No. 5(1993)-9134) had good performance as traction drive fluids for lubrication of traction drive units.

When the hydrogenated oligomer of an unsaturated bicyclo heptane derivative and the hydrogenated oligomer of an unsaturated bicyclo octane derivative described above are produced, it is necessary that, prior to hydrogenation, the unsaturated bicyclo heptane derivative and the unsaturated bicyclo octane derivative should be subjected to oligomerization. The unsaturated bicyclo heptane derivative and the unsaturated bicyclo octane derivative, which are each the raw materials for the oligomers, are obtained from dehydration reactions of respective corresponding alcohols.

During the dehydration reaction of the corresponding alcohol, cyclopentadiene derivatives or cyclohexadiene derivatives inevitably occur as by-products. Therefore, when the unsaturated bicyclo heptane derivative or the unsaturated bicyclo octane derivative, which is obtained from the dehydration reaction of the corresponding alcohol, is subjected to oligomerization, a raw material containing a cyclopentadiene derivative or a cyclohexadiene derivative as the by-products of the dehydration reaction is supplied to the oligomerization step.

However, it has been found that, if a cyclodiene derivative occurring as the by-product of the dehydration reaction is present in the raw material, the oligomerization of the unsaturated bicyclo heptane derivative or the unsaturated bicyclo octane derivative cannot proceed smoothly.

Accordingly, the inventors eagerly carried out study to eliminate the above-described problems.

As a result, it has been found that, in the cases where the formation of the cyclopentadiene derivatives or the cyclohexadiene derivatives as by-products is restricted to at most 1% by weight when the unsaturated bicyclo heptane derivative or the unsaturated bicyclo octane derivative is produced by the dehydration reaction of the corresponding alcohol, and in cases where the thus obtained compound is used as the raw material for the oligomerization, the oligomerization reaction can proceed smoothly. The present invention has been accomplished based on such findings.

SUMMARY OF THE INVENTION

An object of the present invention is to provide a process for efficiently producing an oligomer suitable for use in a traction drive fluid which has a low viscosity and has good performance over a wide temperature range.

The present invention provides a process for producing an oligomer by oligomerizing a raw material comprising an unsaturated bicyclo [2.2.1] heptane derivative and/or an unsaturated bicyclo [2.2.2] octane derivative, which comprises the step of restricting the contents of dienes contained in the raw material to at most 1% by weight.

The present invention also provides a process for producing an oligomer, wherein a raw material comprising an unsaturated bicyclo [2.2.1] heptane derivative and/or an unsaturated bicyclo [2.2.2] octane derivative is subjected to solid acid treatment simultaneously with distillation, or is subjected to solid acid treatment and then to distillation, and is thereafter subjected to oligomerization in sequence.

DESCRIPTION OF THE PREFERRED EMBODIMENTS

The term "unsaturated bicyclo [2.2.1] heptane derivative" as used herein means an unsaturated bicyclo [2.2.1] heptane and/or a derivative thereof (hereinafter sometimes referred to as bicyclo heptanes). In the process of the present invention, the unsaturated bicyclo [2.2.1] heptane derivative in the raw material to be subjected to oligomerization may be produced by any method. However, in general, it is produced by a dehydration reaction of the corresponding alcohol. It is produced such that the formation of dienes as decomposition by-products may be restricted to at most 1% by weight.

Examples of the unsaturated bicyclo [2.2.1] heptane derivatives include bicyclo [2.2.1] hept-2-ene, 2-methylenebicyclo [2.2.1] heptane, 2-methylbicyclo [2.2.1] hept-2ene, 2-methylene-3-methylbicyclo [2.2.1] heptane, 2,3dimethylbicyclo [2.2.1] hept-2-ene, 2-methylene-7- methylbicyclo [2.2.1] heptane, 2,7-dimethylbicyclo [2.2.1] hept-2-ene, 2-methylene-5-methylbicyclo [2.2.1] heptane, 2,5- dimethylbicyclo [2.2.1] hept-2-ene, 2-methylene-6- methylbicyclo [2.2] heptane, 2,6-dimethylbicyclo 2.2.1] hept-2-ene, 2-methylene-1-methylbicyclo [2.2.1] heptane, 1,2- dimethylbicyclo [2.2.1] hept-2-ene, 2-methylene-4 -methylbicyclo [2.2.1] heptane, 2,4-dimethylbicyclo [2.2.1] hept-2-ene, 2-methylene-3,7-dimethylbicyclo [2.2.1] heptane, 2,3,7-trimethylbicyclo [2.2.1] hept-2-ene, 2-methylene-3,6-dimethylbicyclo [2.2.1] heptane, 2,3,6-trimethylbicyclo [2.2.1] hept-2-ene, 2-methylene-3-ethylbicyclo [2.2.1] heptane, and 2-methyl-3-ethylbicyclo [2.2.1] hept-2-ene.

Also, the term "unsaturated bicyclo [2.2.2] octane derivative" as used herein means an unsaturated bicyclo [2.2.2] octane and/or a derivative thereof (hereinafter sometimes referred to as bicyclo octanes). In the process of the present invention, the unsaturated bicyclo [2.2.2] octane derivative, which is contained in the raw material to be subjected to oligomerization, is an unsaturated compound generally produced by a dehydration reaction of the corresponding alcohol derivative.

Examples of the unsaturated bicyclo [2.2.2] octane derivatives include bicyclo [2.2.2] oct-2-ene, 2-methylenebicyclo [2.2.2] octane, 2-methylbicyclo [2.2.2] oct-2-ene, 2-methylene-3-methylbicyclo [2.2.2] octane, and 2,3-dimethylbicyclo [2.2.2] oct-2-ene.

The unsaturated bicyclo [2.2.1] heptane and derivatives thereof and the unsaturated bicyclo [2.2.2] octane and derivatives thereof are ordinarily obtained in the manner described below.

Specifically, first, a cyclodiene is reacted with an aldehyde or an alcohol. Thereafter, the resulting reaction product is cooled and subjected to hydrogenation in the presence of a catalyst (e.g. a Raney nickel catalyst). After cooling, the catalyst is removed by filtration, the filtrate is distilled under reduced pressure, and the corresponding alcohol derivative is thereby formed.

Examples of the cyclodienes include cyclopentadiene, dimethylcyclopentadiene, methylcyclopentadiene, cyclohexadiene, methylcyclohexadiene, and derivatives of these compounds. Examples of the derivatives of these compounds include dicyclopentadiene, a methylcyclopentadiene dimer, and a dimethylcyclopentadiene dimer.

Examples of the aldehydes include crotonaldehyde and acrolein (acrylic aldehyde).

The alcohol is, for example, allyl alcohol.

In the present invention, the unsaturated bicyclo [2.2.1] heptane derivatives and the unsaturated bicyclo [2.2.2] octane derivatives may be used in combination. In such cases, cyclodienes may be reacted with aldehydes and alcohols, and the resulting reaction product may be processed in the same manner as described above.

The corresponding alcohol, which has been obtained in the manner described above, may then be subjected to a dehydration reaction in the presence of a catalyst in order to yield the unsaturated bicyclo [2.2.1] heptane derivative or the unsaturated bicyclo [2.2.2] octane derivative. During the dehydration reaction, cyclopentadiene derivatives or cyclohexadiene derivatives are formed as by-products. The formation of the by-products should be restricted to at most 1% by weight.

As the catalyst to be used in the dehydration reaction, any of the following may be used: a metal oxide such as alumina, titania, chromia, magnesia, or silica-alumina; a metal phosphate such as calcium phosphate, zirconium phosphate, or calcium hydroxy-apatite; a metal sulfate such as magnesium sulfate, calcium sulfate, or aluminum sulfate; and a lamellar silicate such as zeolite, bentonite, montmorillonite, or kaolin. Among these catalysts, $\gamma$-alumina undergoing little skeleton isomerization is preferably used.

When the dehydration reaction is carried out by using such a catalyst, the reaction conditions may vary depending on the combination of a reaction temperature and a weight hourly space velocity (WHSV). The reaction temperature falls within the range of ordinarily 50° to 400° C., preferably 100° to 350° C., more preferably 200° to 340° C.

The WHSV falls within the range of ordinarily 0.1 to 10.0 $hr^{-1}$, preferably 0.5 to 5.0 $hr^{-1}$, more preferably 0.6 to 4.0 $hr^{-1}$.

The unsaturated bicylco [2.2.1] heptane derivative and the unsaturated bicyclo [2.2.2] octane derivative may be obtained under any of reaction conditions. However, it is essential that the contents of dienes as by-products of the dehydration reaction should be restricted to at most 1% by weight.

In order to restrict the contents of dienes as by-products of the dehydration reaction to at most 1% by weight, for example, before the raw material comprising the unsaturated bicyclo [2.2.1] heptane derivative and/or the unsaturated bicyclo [2.2.2] octane derivative is subjected to oligomerization, the raw material is subjected to solid acid treatment simultaneously with distillation, or is sequentially subjected to solid acid treatment and then to distillation.

Examples of solid acids to be used during the solid acid treatment include activated clay, acid clay, zeolite, silica, alumina, silica-alumina, a cation exchange resin, and a heteropolyacid.

The solid acid is used in a proportion falling within the range of 0.01 to 100% by weight, preferably 0.1 to 20% by weight based on the unsaturated bicyclo [2.2.1] heptane derivative and/or the unsaturated bicyclo [2.2.2] octane derivative.

The treatment temperature may be determined appropriately in accordance with the kind of the solid acid used, and falls within the range of ordinarily 0° to 250° C., preferably 50° to 150° C.

The distillation preceding the oligomerization may be carried out in a different treatment vessel after the solid acid treatment has been carried out. Alternatively, the distillation may be carried out simultaneously with the solid acid treatment in the same treatment vessel as that for the solid acid treatment. From the viewpoint of the production efficiency, the solid acid treatment and the distillation should preferably be carried out simultaneously with each other. The distillation may be carried out under reduced pressure or atmospheric pressure.

The solid acid may be kept in the treatment vessel and used many times repeatedly insofar as its effect persists.

Also, the obtained olefin may be subjected to superfractionation to restrict the contents of the by-products to at most 1% by weight.

In the present invention, the oligomer can be obtained efficiently in the case where the raw material is subjected to the solid acid treatment, to the distillation, and thereafter to the oligomerization in sequence.

Specifically, the unsaturated bicyolo [2.2.1] heptane derivative and/or the unsaturated bicyclo [2.2.2] octane derivative, which has been subjected to the solid acid treatment and then to the distillation, is thereafter oligomerized.

Thereafter, the oligomer which has been obtained from the oligomerization, is hydrogenated. The hydrogenated oligomer thus obtained is preferably used in traction drive fluids.

The oligomerization reaction of the raw material olefin is carried out in the presence of a catalyst and, when necessary, by the addition of a solvent or a reaction controlling agent. As the catalyst, various compounds may be used, of which an acid catalyst is ordinarily employed.

Examples of the acid catalysts include a clay such as activated clay or acid clay; a mineral acid such as sulfuric acid or hydrochloric acid; an organic acid such as p-toluenesulfonic acid or triflic acid; a Lewis acid such as aluminum chloride, ferric chloride, stannic chloride, titanium trichloride, titanium tetrachloride, boron trifluoride, hydrogen fluoride, boron tribromide, aluminum bromide, gallium chloride, or gallium bromide; and a solid acid such as zeolite, silica, alumina, silica-alumina, a cationic ion exchange resin, or a heteropolyacid. An appropriate acid catalyst may be selected by considering the easiness of handling and economical efficiency. Though not limited to a specific value, the proportion of the acid catalyst used is ordinarily 0.1 to 100% by weight, preferably 1 to 20% by weight, based on the raw material such as bicyclo octanes or bicyclo heptanes.

During the oligomerization or the cooligomerization of the unsaturated bicyclo [2.2.1 ] heptane derivative and/or the unsaturated bicyclo [2.2.2 ] octane derivative, solvents are not necessarily used, but should preferably be used in order to facilitate the handling of the bicyclo heptanes, the bicyclo octanes, and the catalyst when the reaction is carried out, or to regulate the progress of the reaction.

The solvent to be used for such purposes may be selected arbitrarily from, for example, a wide variety of saturated hydrocarbons such as n-pentane, n-hexane, heptane, octane, nonane, decane, cyclopentane, cyclohexane, methylcyclohexane, and decalin. Also, in the case where the catalyst such as clays having low reaction activity is used as the above-described catalyst, an aromatic hydrocarbon such as benzene, toluene, xylene, or tetralin may be employed as the solvent. A mineral oil (150 neutral, 500 neutral, or the like) may also be used as the solvent.

The reaction controlling agent is used in order to cause the bicyclo heptanes or the bicyclo octanes to undergo an adequate degree of reaction, in particular, in order to increase the selectivity in the oligomerization or cooligomerization reaction of the dimerization or codimerization reaction. The reaction controlling agent is used in a proportion falling within the range of ordinarily 0.1 to 100% by weight, preferably 0.5 to 20% by weight based on the amount of the catalyst used.

Examples of the reaction controlling agent include a carboxylic acid such as acetic acid; an acid anhydride such as acetic anhydride or phthalic anhydride; a cyclic ester such as γ-butyrolactone or valerolactone; a glycol such as ethylene glycol; an ester such as ethyl acetate; a ketone such as mesityl oxide; an aldehyde such as formalin or acetaldehyde; Cellosolve, and water.

The conditions of the above-mentioned reaction art set appropriately in accordance with the kinds of the catalyst and additives. In general, the reaction temperature falls within the range of −30° C. to +300° C. For example, in the case where a clay or zeolite is used as the catalyst, the reaction is carried out at a temperature within the range of room temperature to 250° C., preferably at 60° C. or higher. In the case where other kinds of catalysts are used, the reaction is carried out at a temperature within the range of −30° to +100° C., preferably 0° to 60° C.

During the oligomerization or cooligomerization reaction, heavy fractions such as trimers or higher oligomers are produced as the by-products. These heavy fractions are hydrogenated for use as a viscosity controlling agent or a traction coefficient controlling agent.

The hydrogenated product of the oligomer or the cooligomer, i.e. the hydrocarbon having a bicyclo heptane skeleton or a bicyclo octane skeleton, may be used alone as a traction drive fluid. Alternatively, when necessary, the hydrogenated product of the oligomer or the cooligomer may be mixed with other traction drive fluid for use as a mixture. In such cases, the content of the hydrogenated dimer is not specifically limited, but may be selected appropriately in accordance with the kind of the hydrogenated product of the oligomer, the kinds of the other traction drive fluids to be added, and the like. It is desirable that the hydrogenated product of the oligomer be contained in a proportion of at least 5% by weight, preferably at least 30% by weight based on the total amount of the traction drive fluid.

Examples of the other traction drive fluids that are to be mixed with the traction drive fluid from the oligomer product obtained in accordance with the present invention include the fluids which are conventionally utilized as traction drive fluids, and oils that have not been put to practical use alone as the traction drive fluid because of their low traction performance. Specifically, the other traction drive fluids include a wide variety of liquids, e.g. mineral oils such as paraffinic mineral oils, naphthenic mineral oils; alkyl benzenes, polybutenes, poly-α-olefins, synthetic naphthenes, esters, and ethers.

Among the above-enumerated liquids, alkyl benzenes, polybutenes, and synthetic naphthenes are preferable. Examples of the synthetic naphthenes include alkane derivatives having at least two cyolohexane rings, alkane derivatives having at least one decalin ring at least one cyclohexane ring, alkane derivatives having at least two decalin rings, compounds having structures in which at least two cyclohexane rings or decalin rings are directly linked with each other, alkane derivatives having at least two norbornane rings, and compounds having structures in which at least two norbornane rings are directly linked with each other. Specifically, such synthetic naphthenes include 1-cyclohexyl-1-decalylethane, 1,3-dicyclohexyl-3-methylbutane, 2,4-dicyclohexylpentane, 1,2-bis(methylcyolohexyl)-2-methylpropane, 1,1-bis(methylcyclohexyl)-2-methylpropane, 2,4-dicyclohexyl-2-methylpentane, and 1,3-bis(bicyclo [2.2.1]heptyl) butane.

The traction drive fluid constituted of the oligomer product obtained in accordance with the present invention contains the hydrogenated hydrocarbon having a bicyclo heptane or bicyclo octane skeleton as the essential component. Optionally, this traction drive fluid may be blended with other liquids (traction drive fluids, and the like). Also, when necessary, a variety of additives may be incorporated therein in appropriate amounts. Examples of such additives include antioxidants, rust preventives, detergent dispersants, pour point depressants, viscosity index improvers, extreme pressure agents, antiwear agents, fatigue preventing agents, antifoam agents, oiliness improvers, and colorants.

As described above, with the process in accordance with the present invention, an oligomer suitable for use in a traction drive fluid can be produced with a very high yield from the raw material comprising an unsaturated bicyclo [2.2.1] heptane derivative and/or an unsaturated bicyclo [2.2.2] octane derivative.

Therefore, the oligomer obtained in accordance with the present invention can be utilized widely as a material for traction drive fluids which are to be used in continuously variable transmission for automobiles and for industrial purposes, hydraulic machines, and a variety of other appliances.

The present invention will herein below be described in further detail with reference to the following non-limitative examples and comparative examples.

COMPARATIVE EXAMPLE 1

After 561 g (8 mols) of crotonaldehyde and 352 g (2.6 mols) of dicyclopentadiene were introduced into a 2-liter stainless steel autoclave, the resulting mixture was subjected to a reaction at 170° C. for 3 hours.

The reaction mixture was cooled to room temperature, 18 g of a Raney nickel catalyst (M-300T supplied by Kawaken Fine Chemicals Co., Ltd.) was added thereto, and the resulting mixture was hydrogenated under the conditions of a hydrogen pressure of 9 kg/cm$^2$, a reaction temperature of 150° C., and a reaction time of 4 hours. Thereafter, the reaction mixture was cooled, the catalyst was removed by filtration, and the filtrate was distilled under a reduced pressure to obtain 565 g of a 105° C.20 mmHg fraction.

Analysis of the obtained fraction with the mass spectrum and the nuclear magnetic resonance spectrum revealed that this fraction was 2-hydroxymethyl-3-methylbicyclo [2.2.1] heptane.

Thereafter, 20 g γ-alumina (N612N supplied by Nikki Chemical Co., Ltd.) was introduced into an atmospheric pressure flow reactor made of quartz glass having an outer diameter of 20 mm and a length of 500 mm, and the fraction obtained in the manner described above was subjected to dehydration reaction under the conditions of a reaction temperature of 325° C. and a weight hourly space velocity (WHSV) of 1.5 hr$^{-1}$. As a result, there was obtained 490 g of a dehydration product of 2-hydroxymethyl-3-methylbicyclo [2.2.1] heptane containing 2-methylene-3-methylbicyclo [2.2.1] heptane and 2,3-dimethylbicyclo [2.2.1] hept-2-ene.

Into a 1-liter three neck flask, 460 g of the thus obtained dehydration product and 23 g of an activated clay (Galleonite #136 supplied by Mizusawa Industrial Chemicals, Ltd.) were introduced. The resulting mixture was stirred at 140° C. for 3 hours and thus subjected to an oligomerization reaction. The reaction results are given in Tables 1 and 2.

COMPARATIVE EXAMPLE 2

The procedure in Comparative Example 1 was repeated except that the dehydration reaction was carried out at 320° C. The reaction results are given in Table 1.

EXAMPLE 1

The procedure in Comparative Example 1 was repeated except that the dehydration reaction was carried out at a reaction temperature of 300° C. and a WHSV of 1.0 hr$^{-1}$. The reaction results are given in Tables 1 and 2.

EXAMPLE 2

The procedure in Comparative Example 1 was repeated except that the dehydration reaction was carried out at 290° C. The reaction results are given in Table 1.

EXAMPLE 3

The procedure in Comparative Example 1 was repeated except that the dehydration reaction was carried out at 300° C. The reaction results are given in Table 1.

EXAMPLE 4

The procedure in Comparative Example 1 was repeated except that the dehydration reaction was carried out at 315° C. The reaction results are given in Table 1.

EXAMPLE 5

The procedure in Comparative Example 1 was repeated except that the dehydration reaction was carried out at a reaction temperature of 315° C. and a WHSV of 2.0hr$^{-1}$. The reaction results are given in Table 1.

EXAMPLE 6

The procedure in Comparative Example 1 was repeated except that the dehydration reaction was carried out at a WHSV of 2.0 hr$^{-1}$. The reaction results are given in Table 1.

COMPARATIVE EXAMPLE 3

The procedure in Comparative Example 1 was repeated except that the dehydration reaction was carried out at a reaction temperature of 335° C. and a WHSV of 2.0 hr$^{-1}$. The reaction results are given in Table 1.

COMPARATIVE EXAMPLE 4

2-Hydroxymethylbicyclo [2.2.1 ] heptane was obtained in an amount of 420 g in the same manner as in Comparative Example 1, except that 522 g of allyl alcohol was used in lieu of 561 g of crotonaldehyde, and 396 g of dicyclopentadiene was used.

The thus obtained compound was subjected to the dehydration reaction followed by the oligomerization reaction in the same manner as in Comparative Example 1. The reaction results are given in Tables 1 and 2.

EXAMPLE 7

The procedure in Comparative Example 4 was repeated except that the dehydration reaction was carried out at 290° C. The reaction results are given in Table 1.

COMPARATIVE EXAMPLE 5

2-Hydroxymethylbicyclo [2.2.1] octane was obtained in an amount of 515 g in the same manner as in Comparative Example 1, except that 362 g of acrolein was used in lieu of 561 g of crotonaldehyde, and 400 g of 1,3-cyclohexadiene was used in lieu of 396 g of dicyclopentadiene.

The thus obtained compound was processed in the same manner as in Comparative Example 1. The reaction results are given in Tables 1 and 2.

EXAMPLE 8

The procedure in Comparative Example 5 was repeated except that the dehydration reaction was carried out at 290° C. The reaction results are given in Table 1.

TABLE 1

| | Contents of dienes (% by weight) | Yield of oligomer (%) Dimer | Trimer |
| --- | --- | --- | --- |
| Comparative Example 1 | 1.8 | 4.0 | — |
| Comparative Example 2 | 1.4 | 17.6 | 0.5 |
| Example 1 | 0.7 | 52.7 | 7.1 |
| Example 2 | 0.1 | 55.5 | 8.4 |
| Example 3 | 0.2 | 57.0 | 7.9 |
| Example 4 | 0.8 | 50.2 | 6.5 |
| Example 5 | 0.4 | 53.4 | 5.7 |
| Example 6 | 0.7 | 51.6 | 6.4 |
| Comparative Example 3 | 1.6 | 10.0 | 0.7 |
| Comparative Example 4 | 1.3 | 12.3 | 0.9 |
| Example 7 | 0.4 | 55.2 | 9.4 |
| Comparative Example 5 | 1.1 | 16.2 | 1.8 |
| Example 8 | 0.2 | 53.4 | 9.6 |

EXAMPLE 9

The procedure in Comparative Example 1 was repeated except that 490 g of the olefin which had been obtained in the same manner as in Comparative Example 1, and 5 g of activated clay were introduced into a 1-liter three neck flask, the resulting mixture was stirred at 100° C. for 1 hour, and thereafter subjected to simple distillation under a reduced pressure of 100 mmHg to produce 460 g of an olefin, which was used for the reactions. The reaction results are given in Table 2.

EXAMPLE 10

The procedure in Comparative Example 2 was repeated except that 490 g of the olefin which had been obtained in the same manner as in Comparative Example 2, and 5 g of activated clay were introduced into a 1-liter three neck flask, the resulting mixture was stirred at 100° C. for 1 hour, and thereafter subjected to simple distillation under a reduced pressure of 100 mmHg to produce 460 g of an olefin, which was used for the reactions. The reaction results are given in Table 2.

EXAMPLE 11

The procedure in Comparative Example 4 was repeated except that 355 g of the olefin which had been obtained in the same manner as in Comparative Example 4, and 5 g of activated clay were introduced into a 1-liter three neck flask, the resulting mixture was stirred at 100° C. for 1 hour, and thereafter subjected to simple distillation under a reduced pressure of 100 mmHg to produce 340 g of an olefin, which was used for the reactions. The reaction results are given in Table 2.

EXAMPLE 12

The procedure in comparative Example 5 was repeated except that 430 g of the olefin which had been obtained in the same manner as is Comparative Example 5, and 5 g of activated clay were introduced into a 1-liter three neck flask, the resulting mixture was stirred at 100° C. for 1 hour, and thereafter subjected to simple distillation under a reduced pressure of 100 mmHg to produce 400 g of an olefin, which was used for the reactions. The reaction results are given in Table 2.

COMPARATIVE EXAMPLE 6

2-Hydroxymethyl-methylbicyclo [2.2.1] heptane was obtained in an amount of 570 g in the same manner as in Comparative Example 1, except that 522 g of allyl alcohol was used in lieu of 561 g of crotonaldehyde, and 480 g of a methylcyclopentadiene dimer was used in lieu of 396 g of dicyclopentadiene.

The thus obtained compound was subjected to the dehydration reaction followed by the oligomerization reaction in the same manner as in Comparative Example 1. The reaction results are given in Table 2.

EXAMPLE 13

The procedure in Comparative Example 6 was repeated except that 490 g of the olefin which had been obtained in the same manner as in Comparative Example 6, and 5 g of activated clay were introduced into a 1-liter three neck flask, the resulting mixture was stirred at 100° C. for 1 hour, and thereafter subjected to simple distillation under a reduced pressure of 100 mmHg to produce 460 g of an olefin, which was used for the reaction. The reaction results are given in Table 2.

COMPARATIVE EXAMPLE 7

The olefin which had been obtained in the same manner as in Comparative Example 1, and 5 g of a catalyst comprising phosphotungstic acid (supplied by Nippon Inorganic Colour & Chemical Co., Ltd.) supported on a silica gel (CA-10 supplied by Fuji Davison Chemical, Ltd.) in an amount of 20% by weight, were introduced into an atmospheric flow reactor made of quartz glass having an outer diameter of 20 mm and a length of 500 mm. A dimerization reaction was carried out at a reaction temperature of 110° C. and a WHSV of 0.80 hr$^{-1}$. The reaction results are given in Table 2.

EXAMPLE 14

The procedure in Comparative Example 7 was repeated except that 490 g of the olefin which had been obtained in the same manner as in Comparative Example 1 and 5 g of activated clay were introduced into a 1-liter three neck flask, the resulting mixture was stirred at 100° C. for 1 hour, and thereafter subjected to simple distillation under a reduced pressure of 100 mmHg to produce 460 g of an olefin, which was used for the reactions. The reaction results are given in Table 2.

COMPARATIVE EXAMPLE 8

The procedure in Comparative Example 7 was repeated except that the oligomerization reaction was carried out by using 5 g of activated clay (Galleonite #136 supplied by Mizusawa Chemical Co., Ltd.) in lieu of 5 g of a catalyst comprizing phosphotungustic acid (supplied by Nippon Inorganic Colour & Chemical Co., Ltd.) supported on a silica gel (CA-10 supplied by Fuji-Davison Chemical, Ltd.) in an amount of 20% by weight. The reaction results are given in Table 2.

EXAMPLE 15

The procedure in Comparative Example 8 was repeated except that 490 g of the olefin which had been obtained in the same manner as in Comparative Example 1, and 5 g of activated clay were introduced into a 1-liter three neck flask, the resulting mixture was stirred at 100° C. for 1 hour, and thereafter subjected to simple distillation under a reduced pressure of 100 mmHg to produce 460 g of olefin, which was used for the reactions. The reaction results are given in Table 2.

COMPARATIVE EXAMPLE 9

The procedure in Comparative Example 7 was repeated except that the oligomerization reaction was carried out by using 5 g of silica-alumina (N632L supplied by Nikki Chemical Co., Ltd.) in lieu of 5 g of a catalyst comprizing phosphotungstic acid (supplied by Nippon Inorganic Colour & Chemical Co., Ltd.) supported on a silica gel (CA-10 supplied by Fuji Davison Chemical, Ltd.) in an amount of 20% by weight. The reaction results are given in Table 2.

EXAMPLE 16

The procedure in Comparative Example 9 was repeated except that 490 g of the olefin which had been obtained in the same manner as in Comparative Example 1, and 5 g of activated clay were introduced into a 1-liter three neck flask, the resulting mixture was stirred at 100° C. for 1 hour, and thereafter subjected to simple distillation under a reduced pressure of 100 mmHg to produce 460 g of olefin, which was used for the reactions. The reaction results are given in Table 2.

TABLE 2

| | Contents of dienes (% by weight) | Yield of oligomer (%) | |
| --- | --- | --- | --- |
| | | Dimer | Trimer |
| Comparative Example 1 | 1.8 | 4.0 | — |
| Example 9 | 0.1> | 55 | 7 |
| Comparative Example 2 | 1.4 | 17.6 | 0.5 |
| Example 10 | 0.1> | 56 | 7 |
| Comparative Example 4 | 1.3 | 12.3 | 0.9 |
| Example 11 | 0.1> | 59 | 9 |
| Comparative Example 5 | 1.1 | 16.2 | 1.8 |
| Example 12 | 0.1> | 42 | 7 |
| Comparative Example 6 | 1.7 | 7 | — |
| Example 13 | 0.1> | 51 | 10 |
| Comparative Example 7 | 1.8 | 1.0> | — |

TABLE 2-continued

| | Contents of dienes (% by weight) | Yield of oligomer (%) | |
| --- | --- | --- | --- |
| | | Dimer | Trimer |
| Example 14 | 0.1> | 54 | 6 |
| Comparative Example 8 | 1.8 | 1.0> | — |
| Example 15 | 0.1> | 52 | 6 |
| Comparative Example 9 | 1.8 | 1.0> | — |
| Example 16 | 0.1> | 51 | 5 |

What is claimed is:

1. A process for producing an oligomer by oligomerizing a raw material comprising a mono-unsaturated bicyclo [2.2.1] heptane, which comprises the step of restricting the contents of dienes contained in said raw material to at most 1% by weight.

2. A process for producing an oligomer by oligomerizing a raw material comprising a mono-unsaturated bicyclo [2.2.2] octane, which comprises the step of restricting the content of dienes contained in said raw material to at most 1% by weight.

3. A process for producing an oligomer by oligomerizing a raw material comprising a mono-unsaturated unsaturated bicyclo [2.2.1] heptane and mono-saturated bicyclo[2.2.2] octane, which comprises the step of restricting the contents of dienes contained in said raw material to at most 1% by weight.

4. The process as claimed in claim 1 wherein the raw material is subjected to solid acid treatment simultaneously with distillation, and is thereafter subjected to oligomerization.

5. The process as claimed in claim 2 wherein the raw material is subjected to solid acid treatment simultaneously with distillation, and is thereafter subjected to oligomerization.

6. The process as claimed in claim 3 wherein the raw material is subjected to solid acid treatment simultaneously with distillation, and is thereafter subjected to oligomerization.

7. The process as claimed in claim 1 wherein the raw material is subjected to solid acid treatment, to distillation, and thereafter to oligomerization in sequence.

8. The process as claimed in claim 2 wherein the raw material is subjected to solid acid treatment, to distillation, and thereafter to oligomerization in sequence.

9. The process as claimed in claim 3 wherein the raw material is subjected to solid acid treatment, to distillation, and thereafter to oligomerization in sequence.

* * * * *